(12) United States Patent
Petersen et al.

(10) Patent No.: US 7,212,847 B2
(45) Date of Patent: May 1, 2007

(54) DELTA-SIGMA MODULATOR FOR OUTPUTTING ANALOG REPRESENTATION OF PHYSIOLOGICAL SIGNAL

(75) Inventors: Ethan Petersen, Castro Valley, CA (US); William Shea, Livermore, CA (US); Bradford B. Chew, San Ramon, CA (US)

(73) Assignee: Nellcor Puritan Bennett LLC, Pleasanton, CA (US)

( * ) Notice: Subject to any disclaimer, the term of this patent is extended or adjusted under 35 U.S.C. 154(b) by 121 days.

(21) Appl. No.: 10/787,853

(22) Filed: Feb. 25, 2004

(65) Prior Publication Data

US 2005/0187453 A1    Aug. 25, 2005

(51) Int. Cl.
*A61B 5/00* (2006.01)
(52) U.S. Cl. .............. 600/323; 600/324; 600/500
(58) Field of Classification Search ........ 600/309, 600/310, 316, 323, 300, 324, 500
See application file for complete search history.

(56) References Cited

U.S. PATENT DOCUMENTS

| | | | |
|---|---|---|---|
| 4,802,486 A | 2/1989 | Goodman et al. | |
| 4,873,987 A * | 10/1989 | Djordjevich et al. | 600/485 |
| 4,911,167 A | 3/1990 | Corenman et al. | |
| 4,928,692 A | 5/1990 | Goodman et al. | |
| 4,934,372 A | 6/1990 | Corenman et al. | |
| 5,061,925 A * | 10/1991 | Sooch et al. | 341/120 |
| 5,351,685 A | 10/1994 | Potratz | |
| 5,368,026 A | 11/1994 | Swedlow et al. | |
| 5,396,244 A * | 3/1995 | Engel | 341/143 |
| 5,662,106 A | 9/1997 | Swedlow et al. | |
| 5,713,355 A | 2/1998 | Richardson et al. | |
| 5,746,697 A | 5/1998 | Swedlow et al. | |
| 5,803,910 A | 9/1998 | Potratz | |
| 5,921,921 A | 7/1999 | Potratz et al. | |
| 5,924,979 A | 7/1999 | Swedlow et al. | |
| 5,995,858 A | 11/1999 | Kinast | |
| 6,151,516 A | 11/2000 | Kiani-Azarbayjany | |
| 6,226,539 B1 | 5/2001 | Potratz | |
| 6,707,407 B2 * | 3/2004 | Troy et al. | 341/143 |
| 6,924,756 B2 * | 8/2005 | Viswanathan | 341/143 |
| 2002/0077536 A1 | 6/2002 | Diab et al. | |
| 2003/0181798 A1 * | 9/2003 | Al-Ali | 600/324 |

* cited by examiner

Primary Examiner—Eric F. Winakur
(74) Attorney, Agent, or Firm—Fletcher Yoder PC

(57) ABSTRACT

A method and apparatus for providing a substantially real-time representation of an analog representation of a physiological signal is provided. The waveform signal from the sensor is converted into digital form. A delta-sigma modulator is used as a simple Digital-to-analog Converter (DAC). The output can then be provided through a simple hardware filter to give an analog output signal in nearly real-time, which can be used for other instruments, synchronization, display, etc.

19 Claims, 4 Drawing Sheets

DELTA-SIGMA MODULATOR FOR OUTPUTTING ANALOG REPRESENTATION OF PHYSIOLOGICAL SIGNAL

BACKGROUND OF THE INVENTION

The present invention relates to oximeters, and in particular to analog waveform displays in pulse oximeters.

Pulse oximetry is typically used to measure various blood chemistry characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which scatters light through a portion of the patient's tissue where blood perfuses the tissue, and photoelectrically senses the absorption of light in such tissue. The amount of light absorbed at various frequencies is then used to calculate the amount of blood constituent being measured.

The light scattered through the tissue is selected to be of one or more wavelengths that are absorbed by the blood in an amount representative of the amount of the blood constituent present in the blood. The amount of transmitted light scattered through the tissue will vary in accordance with the changing amount of blood constituent in the tissue and the related light absorption. For measuring blood oxygen level, such sensors have typically been provided with a light source that is adapted to generate light of at least two different wavelengths, and with photodetectors sensitive to both of those wavelengths, in accordance with known techniques for measuring blood oxygen saturation.

Known non-invasive sensors include devices that are secured to a portion of the body, such as a finger, an ear or the scalp. In animals and humans, the tissue of these body portions is perfused with blood and the tissue surface is readily accessible to the sensor.

Pulse oximeters, after processing the sensor data and calculating oxygen saturation, present that information to a display. In some pulse oximeters, it is also desirable to display the analog waveform itself. For example, U.S. Pat. No. 6,188,470 shows a signal for a display reflecting the waveform. U.S. Pat. No. 6,385,471 also discusses a waveform display, and sets forth that the data is first digitized, prefiltered, and then reconstructed for the display.

Nellcor Puritan Bennett, the assignee of the present invention, provides analog outputs in a number of its products. The analog outputs are used for such purposes as synchronizing to other instruments (e.g., EKG, multi-parameter monitor) as well as for a display, The analog waveforms are sometimes provided from the hardware pre-processing circuitry, to insure the analog signal is close in time to the actual patient waveform.

A problem with providing an analog waveform to a display after processing is that the processing takes some time, and thus the signal provided is delayed and not real-time.

BRIEF SUMMARY OF THE INVENTION

The present invention provides a method and apparatus for providing a substantially real-time representation of an analog representation of a physiological signal. The waveform signal from the sensor is converted into digital form. A delta-sigma modulator is used as a simple Digital-to-analog Converter (DAC). The output can then be provided through a simple hardware filter to give an analog output signal in nearly real-time, which can be used for other instruments, synchronization, display, etc.

The invention allows a waveform to be converted into digital form, and supplied to the software, while still allowing fast conversion back into hardware after initial processing in software. In particular, for a pulse oximeter that does demodulation in software, the digital IR signal can be obtained after this software demodulation, but before the much slower software filtering process used as part of the process to calculate oxygen saturation.

In one embodiment, in a first path the digital signal is processed, but a second path applies this digitized waveform to the delta-sigma modulator. The second path picks off the signal immediately after it is converted into digital form and demodulated. For a pulse oximeter, an IR signal is chosen for the analog output because it typically has less noise.

In one embodiment, the delta-sigma modulator is a software modulator which operates on the digitized version of the waveform. The delta-sigma modulator provides a single bit, serial output. This output is provided to a hardware RC filter, and then to the display.

For a further understanding of the nature and advantages of the invention, reference should be made to the following description taken in conjunction with the accompanying drawings.

DETAILED DESCRIPTION OF THE INVENTION

Overall System

Figure 1:
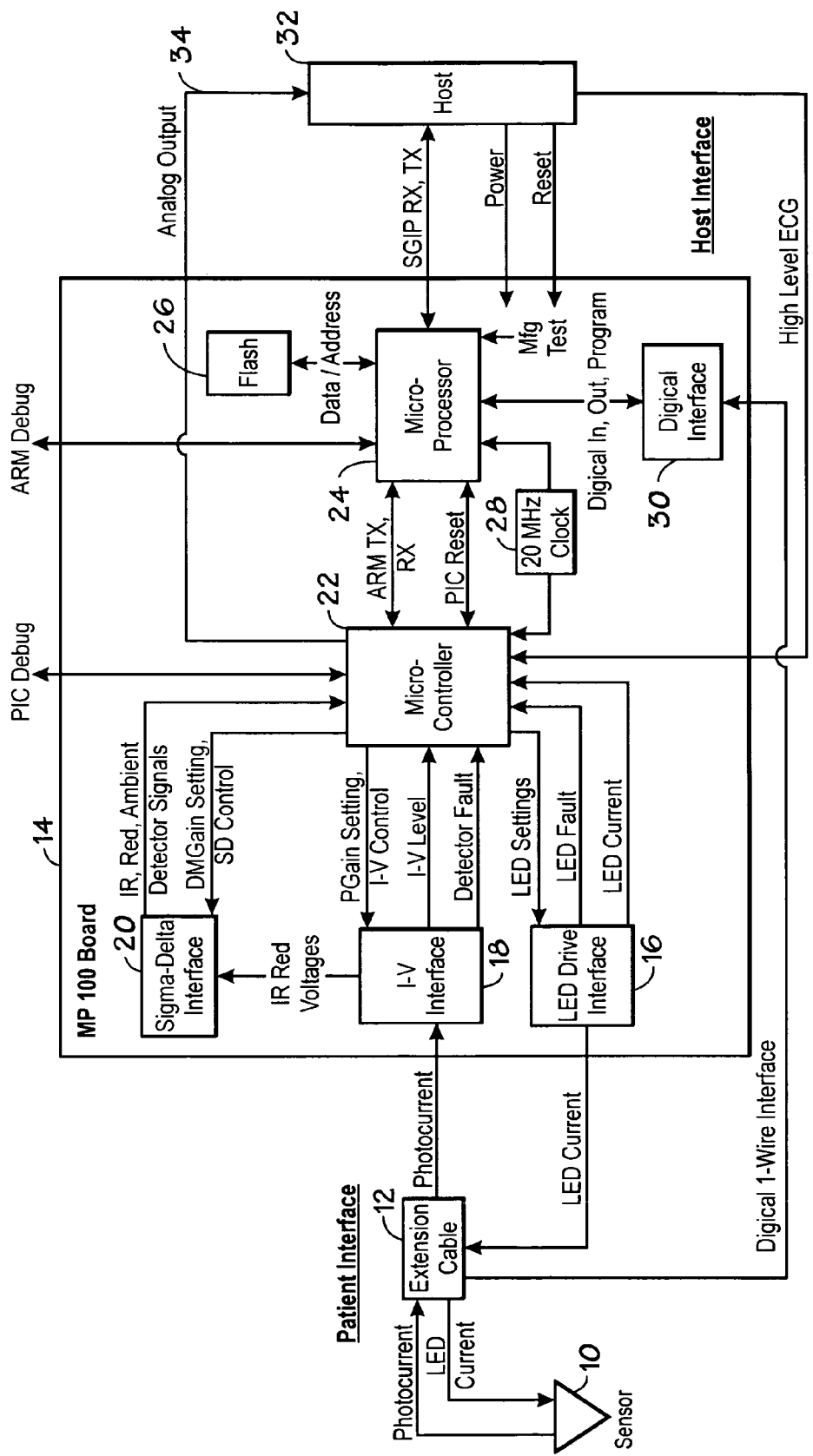
FIG. 1 is a block diagram of an oximeter incorporating the present invention.

FIG. 1 illustrates an embodiment of an oximetry system incorporating the present invention. A sensor 10 includes red and infrared LEDs and a photodetector. These are connected by a cable 12 to a board 14. LED drive current is provided by an LED drive interface 16. The received photocurrent from the sensor is provided to an I-V interface 18. The IR and red voltages are then provided to a sigma-delta interface 20 incorporating the present invention. The output of sigma-delta interface 20 is provided to a microcontroller 22. Microcontroller 22 includes flash memory for a program, and RAM memory for data. The oximeter also includes a microprocessor chip 24 connected to a flash memory 26. Finally, a clock 28 is used and an interface 30 to a digital calibration in the sensor 10 is provided. A separate host 32 receives the processed information, as well as receiving an analog signal on a line 34 for providing an analog display.

Prior Art Demodulation in Hardware

Figure 2:
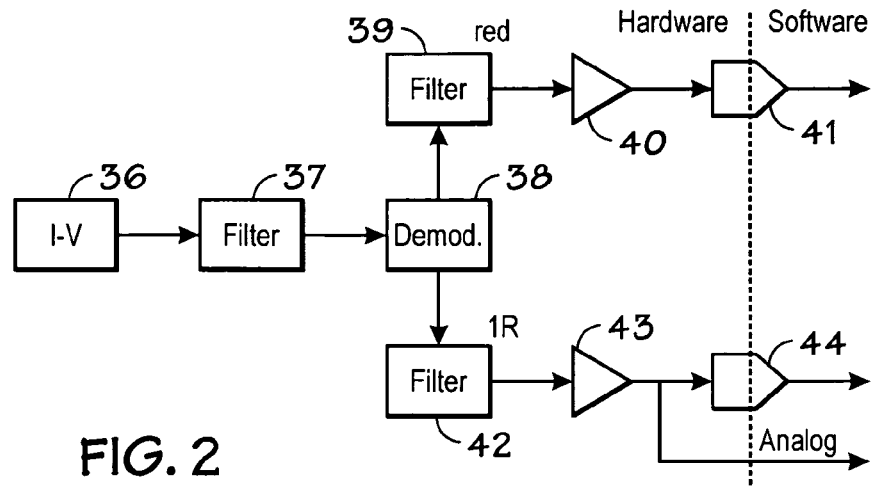
FIG. 2 is a block diagram of a prior art circuit for generating an analog output signal.

FIG. 2 shows an example of a prior art circuit for generating an analog output signal. A signal from a patient sensor is processed in hardware through a current-to-voltage converter (I-V) 36, and a filter 37. The red and IR signals are then demodulated in a demodulator 38. A red signal is provided through a first channel of a filter 39 and an amplifier 40 to an ADC 41. Similarly, the IR signal is provided through a second channel of filter 42, amplifier 43 and ADC 44. The analog output is obtained from the IR signal at the input of ADC 44.

Demodulation in Software in the Present Invention

Figure 3:
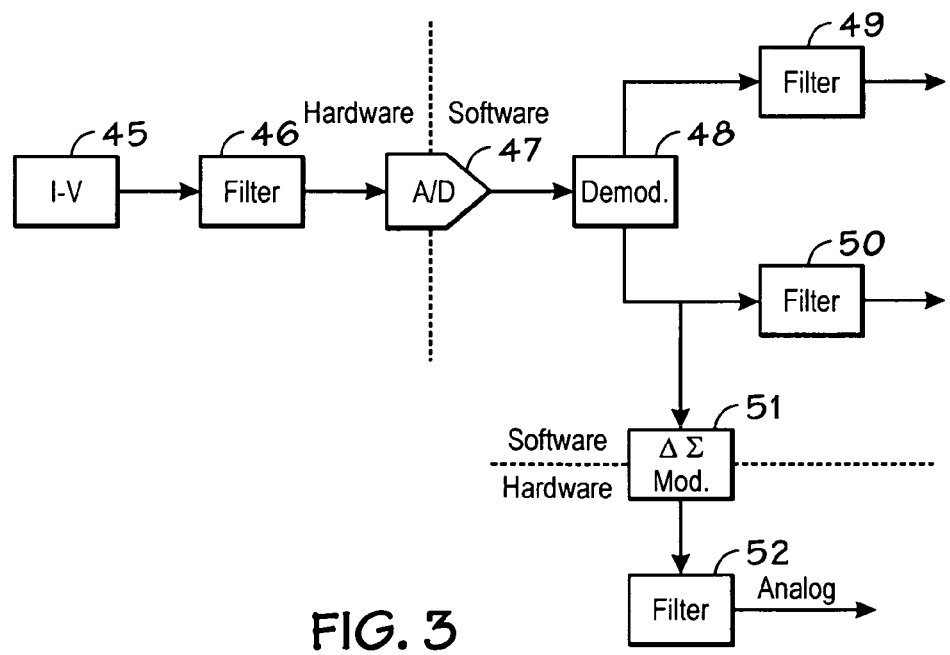
FIG. 3 is a block diagram of an embodiment of a circuit for generating an analog output signal according to the present invention.

FIG. 3 shows an embodiment of the present invention where demodulation isn't done in hardware, rather in software, so an analog IR signal simply is not available in hardware. A signal from a patient sensor is processed in hardware through a current-to-voltage converter 45 and a filter 46, then is supplied to an ADC 47. In software, a demodulator separates the red and IR signals. The red signal is then provided to a software filter 49 and further processing not shown. The IR signal is similarly provided through a software filter 50 and further processing not shown. Since the software filtering can cause a significant time delay, the IR signal before the filter 50 is converted back into analog form. A sigma-delta modulator 51 is used as a simple Digital-to-analog Converter (DAC). By using a sigma-delta modulator, the conversion process is simple and can be done quickly. The resulting analog signal then only needs to be filtered in a simple RC filter 52.

Sigma-Delta Modulator and Filter for Simple DAC

Figure 4:
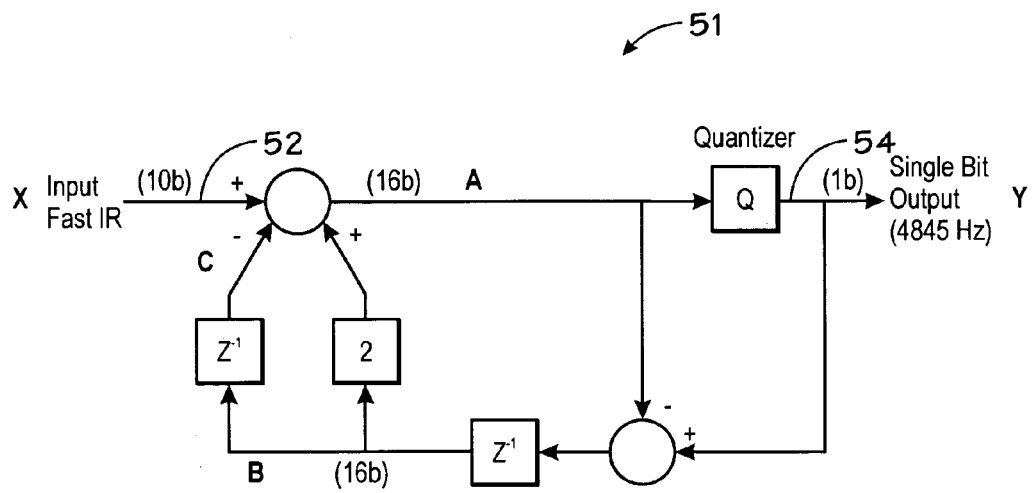
FIG. 4 is a block diagram of the software delta-sigma modulator according to an embodiment of the present invention.

FIG. 4 is a block diagram of a delta-sigma modulator 51 of FIG. 3 according to an embodiment of the invention. This modulator is preferably implemented in software running on microcontroller 22 of FIG. 1. An input on line 52 is the digitized sensor signal. In a preferred embodiment this signal is the infrared (IR) signal as opposed to the red signal. The infrared is chosen because it is typically a cleaner signal than the red signal. FIG. 4 is a graphical representation of the difference equations implemented to create the second order noise shaping for the quintile signal. In one implementation, pseudocode that implements the difference equations is:

```
X is the input on line 52
Y is the output on line 54
A, B, and C are intermediate variables that store data from one iteration to
the next loop every 206 µS
    A = X – C + (2 * B)
    C = B
    if A > ½ then
        Y = 1
    else
        Y = 0
    end if
    B = A – Y
end loop
```

This code is executed in a loop that executes every 206 µS, so the output (Y) is a 4845 bits/sec bit stream with an average value that is equal to the input (X).

Figure 5:
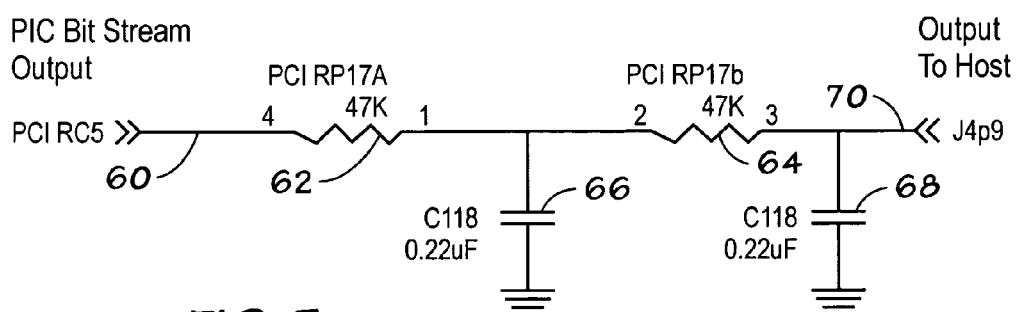
FIG. 5 is a circuit diagram of an embodiment of the hardware RC filter according to an embodiment of the present invention.

The output on line 54 is preferably a 4845 Hz bitstream. This is provided to the input 60 of a hardware filter as shown in FIG. 5. This filter includes resistors 62 and 64 and capacitors 66 and 68. This filter acts on the digital output signal to convert it into analog form to produce an output on line 70 that can be provided to a display. The filter is a passive, second order RC filter, without a buffer on the output. Any buffering could be done by the host system before displaying, if required.

Figure 6:
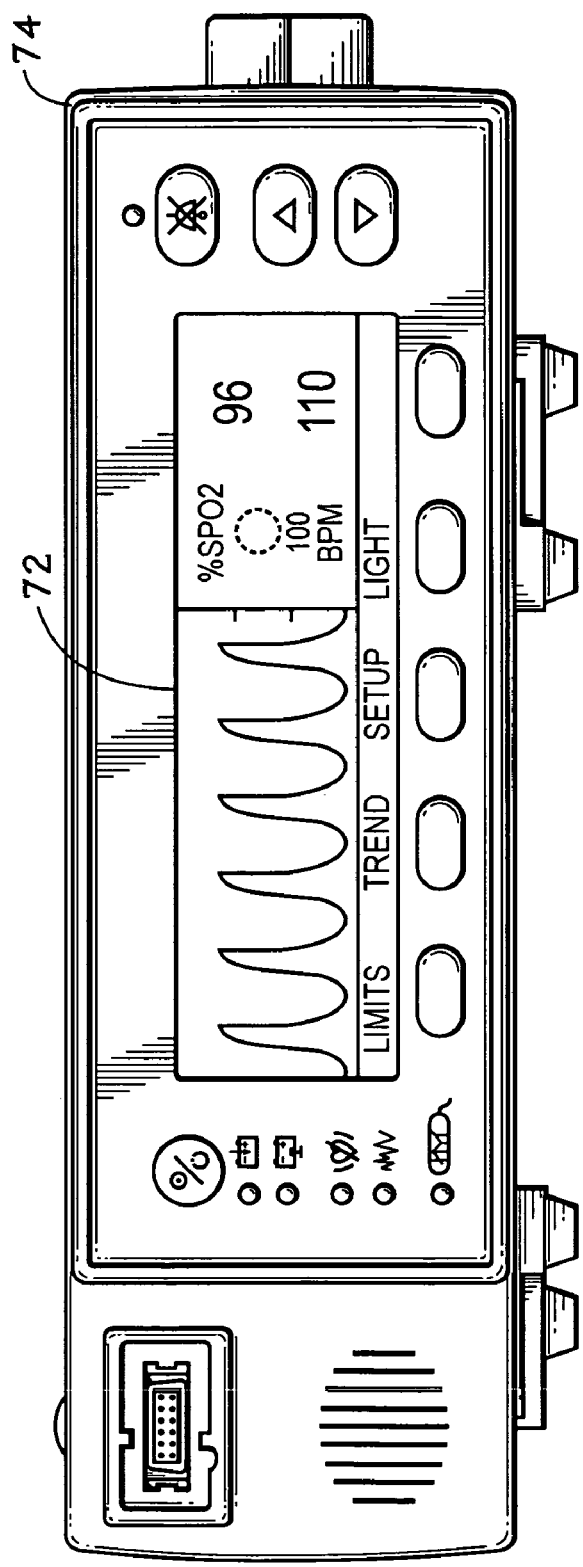
FIG. 6 is a front view of a monitor showing an analog display according to an embodiment of the present invention.

FIG. 6 shows an example of an analog display 72 on a pulse oximeter monitor 74. The signal for this display is provided from line 70 of FIG. 5.

As will be understood by those of skill in the art, the present invention may be embodied in other specific forms without departing from the essential characteristics thereof. For example, the delta-sigma modulator could be of a different order than a second order. Some filtering could be done in software prior to the hardware filter, and a different configuration of the hardware filter could be used. Accordingly, the foregoing description is intended to be illustrative, but not limiting, of the scope of the invention which is set forth in the following claims.

What is claimed is:

1. A method for operating a physiological monitor comprising:
   detecting an analog signal from a patient, wherein the analog signal comprises at least one modulated physiological waveform;
   converting the analog signal into a digital signal;
   demodulating the digital signal to produce at least two demodulated physiological signals;
   applying at least one of the demodulated physiological signals to a delta-sigma modulator to provide at least one physiological waveform; and
   filtering the at least one physiological waveform to provide a real-time analog filtered physiological waveform output, wherein the analog filtered physiological waveform is real-time relative to the time of detecting the analog signal from the patient to the time of providing the analog filtered physiological waveform output.

2. The method of claim 1 wherein filtering at least one physiological waveform comprises passing the at least one physiological waveform through a hardware filter.

3. The method of claim 1 wherein the delta-sigma modulator is configured to provide a single bit output.

4. The method of claim 1, wherein the at least one modulated physiological waveform comprises a representation of an IR signal returned from a physiological sensor and a red signal returned from a physiological sensor.

5. The method of claim 1, wherein converting the analog signal into a digital signal comprises passing the analog signal through an analog-to-digital converter (ADC).

6. The method of claim 1, wherein the demodulated waveform comprises a representation of an IR signal received from a physiological sensor.

7. The method of claim 1, wherein the delta-sigma modulator is configured to provide second order noise shaping of the demodulated physiological signals.

8. The method of claim 1, wherein the delta-sigma modulator is configured to output a serial bit stream having a given frequency.

9. The method of claim 1, wherein the hardware filter comprises an RC filter.

10. A method for operating an oximeter comprising:
    detecting an analog signal from a patient, wherein the analog signal comprises at least one pulse oximetry waveform;
    converting the analog signal into a digital signal;
    demodulating the digital signal to produce a red signal and an IR signal;

applying one of the red signal and the IR signal to a software delta-sigma modulator, wherein the software delta sigma modulator is configured to provide a single bit, serial output; and filtering the single bit, serial output with a hardware filter to provide a real-time analog waveform output, wherein the analog waveform is real-time relative to the time of detecting the analog signal from the patient to the time of providing the analog filtered physiological waveform output.

11. The method of claim 10, wherein the at least one pulse oximetry waveform comprises a representation of an IR signal returned from a physiological sensor or a red signal returned from a physiological sensor.

12. The method of claim 10, comprising configuring the software delta-sigma modulator to provide second order noise shaping of one of the red signal and the IR signal.

13. The method of claim 10, wherein the hardware filter comprises an RC filter.

14. A physiological monitor apparatus comprising:
an input configured to receive an analog signal from a patient, wherein the analog signal comprises a physiological waveform;
an analog-to-digital converter configured to convert the analog signal into a digital form of the physiological waveform;
a processor including a delta-sigma modulator configured to convert the digital form of the physiological waveform into an analog form of the physiological waveform, and wherein the delta-sigma modulator is configured to output the analog form of the physiological waveform; and
a filter configured to receive and filter the analog form of the physiological waveform and to output a real-time waveform, wherein the real-time waveform is real-time relative to the time analog signal received from the patient to the time the real-time waveform is output.

15. The physiological monitor apparatus of claim 14 wherein the delta-sigma modulator comprises a software modulator that produces a serial, single bit output.

16. The physiological monitor apparatus of claim 14 wherein the filter is a hardware RC filter.

17. The method of claim 14, wherein the delta-sigma modulator is configured to output a serial bit stream having a given frequency.

18. An oximeter apparatus comprising:
an input configured to receive a signal, wherein the signal comprises a pulse oximetry waveform, and wherein the pulse oximetry waveform is representative of data gathered from a sensor coupled to a patient;
an analog-to-digital converter configured to convert the pulse oximetry waveform into a digital form of the pulse oximetry waveform;
a processor, comprising:
a demodulator configured to separate the digital form of the pulse oximetry waveform into a red digital signal and an IR digital signal; and
a software delta-sigma modulator configured to convert one of the red digital signal and the IR digital signal into an analog signal, wherein the analog signal is a serial, single bit output;
a hardware RC filter configured to filter the serial, single bit output of the software delta-sigma modulator and to output a filtered signal in real-time, wherein the filtered signal is real-time relative to the time the input receives the signal to the time the filtered signal is output; and
an output configured to provide the real-time filtered signal to a host.

19. The method of claim 18, wherein the serial, single bit output has a given frequency.

* * * * *